(12) United States Patent
Koller et al.

(10) Patent No.: US 7,424,325 B2
(45) Date of Patent: Sep. 9, 2008

(54) PIEZOELECTRICALLY STIMULATED ARTICLE

(76) Inventors: Levente Lajos Koller, 20 Columbia Valley Rd., Andover, NJ (US) 07821; Thomas Bradley Borne, 709 First St., Westfield, NJ (US) 07821

( * ) Notice: Subject to any disclaimer, the term of this patent is extended or adjusted under 35 U.S.C. 154(b) by 212 days.

(21) Appl. No.: 11/098,646

(22) Filed: Apr. 4, 2005

(65) Prior Publication Data
US 2006/0224214 A1    Oct. 5, 2006

(51) Int. Cl.
A61N 1/00    (2006.01)
A61N 1/02    (2006.01)
A61N 1/378    (2006.01)

(52) U.S. Cl. .......................... 607/35; 607/143
(58) Field of Classification Search .............. 607/35, 607/143
See application file for complete search history.

(56) References Cited

U.S. PATENT DOCUMENTS

| | | | |
|---|---|---|---|
| 2,295,585 A | 9/1942 | Lindquist | |
| 3,718,132 A | 2/1973 | Holt et al. | 128/1 C |
| 3,880,170 A | 4/1975 | Popov | 128/421 |
| 3,893,462 A | 7/1975 | Manning | 128/410 |
| 3,946,745 A | 3/1976 | Hsiang-Lai et al. | 128/421 |
| 4,155,366 A | 5/1979 | Di Mucci | 128/421 |
| RE30,366 E * | 8/1980 | Rasor et al. | 607/36 |
| 4,240,437 A | 12/1980 | Church | 128/420 R |
| 4,431,000 A | 2/1984 | Butler et al. | 128/421 |
| 4,541,432 A | 9/1985 | Molina-Negro et al. | 128/421 |
| 4,682,601 A | 7/1987 | Tagliavini | 128/422 |
| 5,070,862 A * | 12/1991 | Berlant | 601/21 |
| 5,431,694 A | 7/1995 | Snaper et al. | 607/35 |
| 5,827,797 A | 10/1998 | Cass et al. | 505/430 |
| 6,246,915 B1 * | 6/2001 | Boutos | 607/143 |
| 6,546,286 B2 | 4/2003 | Olson | 607/5 |
| 6,620,287 B2 | 9/2003 | Cass | 156/295 |
| 2002/0011300 A1 | 1/2002 | Cass | 156/89.12 |
| 2002/0042635 A1 | 4/2002 | Zhang et al. | 607/39 |
| 2004/0072670 A1 | 4/2004 | Kasukawa et al. | 501/134 |
| 2004/0073267 A1 | 4/2004 | Holzer | 607/35 |

OTHER PUBLICATIONS

"Advanced Cerametrics—Piezoelectric Fiber Composites", Apr. 23, 2007, http://www.advancedcerametrics.com/pages/pzt_fiber/.*
F. Mohammadi et al., Mat. Res. Symp. Proc., 736, D5.5.1-D5.5.6 (2003).
M.R. Voegelin et al., Il Nuovo Cimento, 19, No. 6.

* cited by examiner

*Primary Examiner*—Carl H. Layno
*Assistant Examiner*—Yun Haeng Lee
(74) *Attorney, Agent, or Firm*—Sheldon Kavesh

(57) ABSTRACT

Method and self-contained articles for applying to a surface of a human body an electrical potential generated by a piezoelectric element actuated by a motion of a human body.

34 Claims, 5 Drawing Sheets

PIEZOELECTRICALLY STIMULATED ARTICLE

BACKGROUND OF THE INVENTION

1. Field of the Invention

The invention relates to self-contained articles and methods for applying to a surface of a human body an electrical potential generated by a piezoelectric element actuated by a motion of a human body. The articles are useful for augmenting, reducing or eliminating the need to take certain medications, to increase the effectiveness of physical therapy, to reduce pain, to provide stimulation and for other applications.

2. Description of the Related Art

Devices for application of electrical potentials to the surface of a human body is date to at least 1886 and U.S. Pat. No. 334,879. In the intervening century, the science of electrotherapy has been highly improved and devices for its use have become increasingly more sophisticated. Modern applications of electrotherapy include, among others, ionophoresis for transdermal administration of drugs, treatment of pathologies such as cellulitus, electrocicatirization of wounds or injuries to promote healing, and transcutaneous electrical nerve stimulation (TENS) to relieve neurogenic or musculoskeletal pain, or to reduce edema. In a particular area of interest, U.S. Patent Application Publication 2002/0042635 A1 described the use of electrotherapy for the treatment of erectile dysfunction. However, coincident with this progress, electrotherapy devices have also become much more complex.

U.S. Pat. No. 2,295,585 described a device that generated therapeutic current pulses where the pulse rate during active periods could be varied and the length of active and inactive periods could be varied independently. Other devices for creating therapeutic electrical currents of controlled waveform were described in U.S. Pat. Nos. 3,718,132, 3,880,170, 3,893, 462, 3,946,745, 4,155,366, 4,240,437, 4,682,601 and U.S. Patent Application Publications 2003/0191506 A1, and 2003/0195590 A1. U.S. Pat. Nos. 4,431,000 and 4,541,432 described devices that generated pseudo-random pulses. Each of these devices involved complex circuitry and was powered externally or by batteries of limited life that needed periodic replacement.

U.S. Pat. No. 6,546,286 B1 described an electrotherapy device with an external pedal operated power supply. U.S. Pat. No. 5,431,694 described an implanted piezoelectric generator connected to a power-consuming device such as a pacemaker. U.S. Patent Application Publication 2004/0073267 A1 described an implanted micro-electromagnetic generator.

Each of these references represented an advance in the state of the art, however none suggested the devices of this invention, and none satisfies all of the needs met by this invention. A need has long existed for a self-contained electrotherapy device that can be worn on a body, is powered by the motion of a body, is simple, and produces random waveforms without the need for complex circuitry.

SUMMARY OF THE INVENTION

In one embodiment, the invention is a self-contained device for applying an electrical potential to a surface of a human body comprising: a piezoelectric element capable of generating an electrical potential in response to a mechanical stress or strain of the piezoelectric element caused by a motion of a human body; an electrical circuit connected to the piezoelectric element for collection, storage or modification of the electrical potential; and at least two spaced electrodes of opposite polarity for applying the electrical potential to a surface of a human body.

In another embodiment, the invention is an article capable of being worn on a part of a human body selected from the neck, shoulder, elbow, wrist, hand, back, knee, ankle, chest, abdomen, leg and foot comprising the above described device, the piezoelectric element of the device being capable of being mechanically stressed or strained by the motion of the part of the body, and the electrodes of the device capable of being in contact with a human body.

In yet another embodiment, the invention is a method of applying an electrical potential to a surface of human body comprising the steps of: embedding a device as described above in an article, said article capable of being worn in contact with a part of a human body selected from the neck, shoulder, elbow, wrist, hand, back, knee, ankle, chest, abdomen and foot; and placing said article on the body part such that the piezoelectric array of said device is mechanically stressed or strained by the motion of the body part and the electrodes of said device are in electrical contact with a surface of a human body.

DETAILED DESCRIPTION OF THE INVENTION

Figure 1:
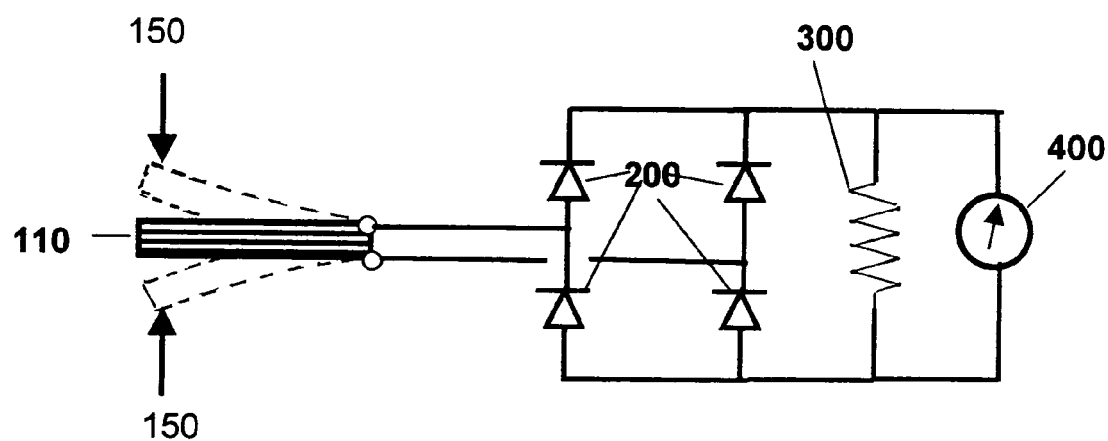
FIG. 1 illustrates a model system used to test the inventive concept.

The invention comprises articles and methods for applying to a surface of a human body an electrical potential generated by a piezoelectric element actuated by a motion of a human body. The articles are useful for augmenting, reducing or eliminating the need to take certain medications, to increase the effectiveness of physical therapy, to reduce pain, to provide stimulation and for other applications.

In one embodiment, the invention is a self-contained device for applying an electrical potential to a surface of a human body comprising: a piezoelectric element capable of generating an electrical potential in response to a mechanical stress or strain of the piezoelectric element caused by a motion of a human body; an electrical circuit connected to the piezoelectric element for collection, storage or modification of the electrical potential; and at least two spaced electrodes of opposite polarity for applying the electrical potential to a surface of a human body. The body activating the piezoelectric element and the body receiving the electrical potential need not be the same body.

A piezoelectric substance is one that produces an electrical charge when a mechanical stress or strain is applied to it. The nature of the stress or strain may be tension, compression or torsion. A number of piezoelectric materials are known. Preferably the piezoelectric element in a device of the invention is comprised of at least one member of the group consisting of PZT (lead zirconium titanate), lead niobate ($PBNbO_6$), barium titanate ($BaTiO_3$), sodium bismuth titanate (pure or co-doped), lead based ceramics doped with lanthanum, tin or niobium, quartz ($SiO_2$), lithium niobate ($LiNbO_3$), lithium tantalate ($LiTaO_3$), polyvinylidene fluoride, polytrifluoroethylene, polytetrafluoroethylene, polyvinylidene cyanide, and polyvinyl acetate.

A method for the preparation of filaments of refractory materials has been described in U.S. Pat. No. 5,827,797. The compositions and preparation of piezoelectric fiber assemblies have been described in U.S. Pat. No. 6,620,287 B2 and U.S. Patent Application Publications 2002/0011300 A1 and 2004/0072670 A1. The disclosures of U.S. Pat. Nos. 5,927,797, 6,620,287 B2 and U.S. Patent Application Publications 2002/0011300 A1 and 2004/0072670 A1 are incorporated herein by reference to the extent not incompatible herewith.

Preferably, the piezoelectric element in a device of the invention is a composite comprised of one or more planar layers of parallel aligned piezoelectric fibers embedded in a matrix. Preferably, the piezoelectric fibers are comprised of at least one member selected from the group consisting of PZT (lead zirconium titanate), lead niobate ($PBNbO_6$), barium titanate ($BaTiO_3$), sodium bismuth titanate (pure or co-doped). Preferably the matrix is one of an elastomeric material having a modulus of elasticity as measured by ASTM D638 less than about 6,000 psi (41.3 MPa), or a rigid polymeric material having a modulus of elasticity as measured by ASTM D638 greater than about 200,000 psi (1,380 MPa). Piezoelectric fiber composites are articles of commerce and may be purchased for example, from Advanced Ceramletrics, Inc., Lambertville, N.J.

Multilayered piezoelectric beams are known as "multimorphs". The layers of a multimorph piezolectric beam may be connected in series or in parallel depending upon whether high voltage (series connection) or high current (parallel connection) is preferred. Voltages of 350 volts were obtained by F. Mohammadi et al., *Mat. Res. Symp. Proc.*, 736, D5.5.1-D5.5.6(2003), and higher voltages up to at least 500 volts are deemed feasible.

The piezoelectric element in a device of the invention is capable of generating a maximum electrical potential of from about 1 to about 500 volts. Preferably, the piezoelectric element is capable of generating a maximum electrical potential of from about 5 volts to about 100 volts. More preferably, the piezoelectric element is capable of generating a maximum electrical potential of from about 10 volts to about 50 volts.

The electrical potential across the electrodes of a device of the invention is preferably from about 10 volts to about 200 volts, more preferably from about 10 volts to about 100 volts, and most preferably from about 10 volts to about 40 volts.

The electrical power the device is capable of delivering to a human body is from about 0.05 milliwatts to about 250 milliwatts, preferably from about 0.05 milliwatts to about 100 milliwatts.

The electrical circuit connecting the piezoelectric element to the electrodes has as its function, the collection, storage and modification of the electrical potential. Design of such circuits are within the ability of one of ordinary skill in the art. Preferably, the output from the piezoelectric element is full-wave rectified by a diode bridge circuit. Preferably, the diodes comprising the full-wave rectifier are of a very low leakage type having a reverse current less than 6.7 picoamperes/volt of reverse potential such as the series CMPD6001S manufactured by Central Semiconductor Corp, Hauppauge N.Y. Particular useful electrical circuits are non-exhaustively illustrated in FIGS. 2-3 and are discussed in the Examples.

Preferably, the electrical circuit connecting the piezoelectric element to the electrodes delivers pulses of electrical energy to the electrodes and to the skin of the human body in contact with the electrodes. The pulses may be of random frequency and amplitude. Preferably, the pulses are of random frequency and constant amplitude. Preferably, the energy delivered per pulse is from about 1 to about 750 microJoules. More preferably, the energy delivered per pulse is from about 1 to about 300 microJoules. Most preferably, the energy delivered per pulse is from about 1 to about 100 microJoules The distance between the electrodes will be governed by the skin impedance of the part of the body, the potential generated by the piezoelectric element and the electrical power it is desired to impart. Preferably, the distance between electrodes of opposite polarity is from about 0.125 inch (0.317 cm) to about 10 inches (25.4 cm). More preferably, the distance between electrodes of opposite polarity is from about 0.25 inch (0.635 cm) to about 5 inches (12.7 cm). Most preferably, the distance between electrodes of opposite polarity is from about 0.375 inch (0.952 cm) to about 2.5 inches (6.35 cm). It is preferable that the distance between electrodes in a device of the invention is adjustable within the given range.

Preferably, electrodes may be easily attached and dis-attached from the device using screw fittings, slip fittings or other means of connecting the electrodes to the device. Electrodes having different shapes and sizes ranging from needle-like forms to conductive pads having dimensions of several inches may be used in different electrotherapy applications. Similarly, the materials of which the electrodes are formed may be of different materials suitable to the use. Electroconductive gels, salt solutions or other materials that improve contact to the surface of the human body may be applied to the electrodes.

However, the surface area of the electrodes should be matched to the power capability of the piezoelectric device. It has been reported in an article by M. R. Voegelin et al., II Nuovo Cimento, 19, No. 6, 1997 that when the electric power dissipated in a stimulated region is within the range of 235-260 mcal/$cm^2$-sec, pain is experienced. Therefore, to be about a factor of two below the threshold of pain, the total surface area of electrodes of a given polarity, measured in square centimeters, should be greater than or equal to 1.9 times the power rating of the piezoelectric element measured in watts.

In a preferred use, a device of the invention is embedded in a latex condom. Pairs of electrodes of opposite polarity are disposed on at least one of the inside surface and the outside surface of the condom. Preferably, the electrodes for this application are comprised of conductive elastomer or conductive plastic film.

In another embodiment, the invention is an article capable of being worn on a part of a human body selected from the neck, shoulder, elbow, wrist, hand, back, knee, ankle, chest, abdomen, leg and foot comprising the above described device, the piezoelectric element of the device being capable of being mechanically stressed or strained by the motion of the part of the body, and the electrodes of the device capable of being in contact with a human body.

Applications of an article of the invention include, among others, iontophoresis for transdermal administration of drugs, treatment of pathologies such as cellulitus, electrocicatirization of wounds or injuries to promote healing, and transcutaneous electrical nerve stimulation (TENS) to relieve neurogenic or musculoskeletal pain, or to reduce edema. In the amelioration of pain arising from joint disease, present battery powered TENS devices deliver electrical stimulation regardless of whether or not the joint is in motion and creating pain. This is a disadvantage as the body may accommodate to the constant electrical stimulation with reduced relief of pain when needed. An advantage of the articles of the invention is that electrical stimulation is provided only when the body is in motion and pain relief may be needed.

The article is preferably a fabric article with the device of the invention attached to the fabric by any conventional means such as sewing, riveting or adhesive bonding. The fabric article can be in the form of a tape or a bandage, or in the form of a garment, such as a shirt or undergarment with the electrodes on the inner surface of the article as normally worn. It is preferred that the fabric portion of the article is an elastic material or an elasticized fabric so as to hold the device snugly to the body. It is also preferred that the ends of a bandage or tape have mating VELCRO® surfaces. In a preferred use, the article is a massage glove with the electrodes on the outside surface of the glove.

In further embodiment, the invention is a method of applying an electrical potential to a surface of human body comprising the steps of embedding a device as described above in an article capable of being worn in contact with a part of a human body selected from the neck, shoulder, elbow, wrist, hand, back, knee, ankle, chest, abdomen, leg and foot; and placing the article on the body part such that the piezoelectric array of the device is mechanically stressed or strained by the motion of the body part and the electrodes of the device are in electrical contact with a surface of a human body.

In yet another embodiment, the invention is a method of applying an electrical potential to a surface of a human body comprising the steps of embedding a device as described above in a condom having an inner and outer surface; and placing the condom on a penis such that the piezoelectric array of said device is mechanically stressed or strained by the act of intercourse and at least two oppositely polarized electrodes of the device are on at least one of the inner or outer surface.

EXAMPLES

Example 1

This example was a test of the inventive concept applied to a model system.

FIG. 1 schematically illustrates the model system having piezoelectric element 110, an electrical circuit connecting the piezoelectric element to a bridge rectifier 200 and then to one megaohm resistor 300 and a voltmeter 400. The piezoelectric element consisted of a bimorph (two layer) PZT (lead zirconium titanate) fiber array having dimensions of 12.7 cm length×1.27 cm width and 0.127 cm thickness obtained from Advanced Cerametrics, Inc., Lambertville, N.J. The piezoelectric fiber array was mounted as a cantilever beam and the free end of the beam was subjected to ±1.90 cm amplitude displacement at a frequency of 10 Hz by a sinusoidal force 150 having a peak amplitude of 227 grams.

The diodes of the rectifier 200 were of a very low leakage type CMPD6001S manufactured by Central Semiconductor Corp, Hauppauge N.Y. The one megaohm resistor simulated the dry skin impedance of a human body.

A full-wave rectified voltage of 50 volts was measured at the voltmeter 400. The power input to the resistor was 1.25 milliwatts. It was concluded that the device concept was valid.

Example 2

Figure 2:
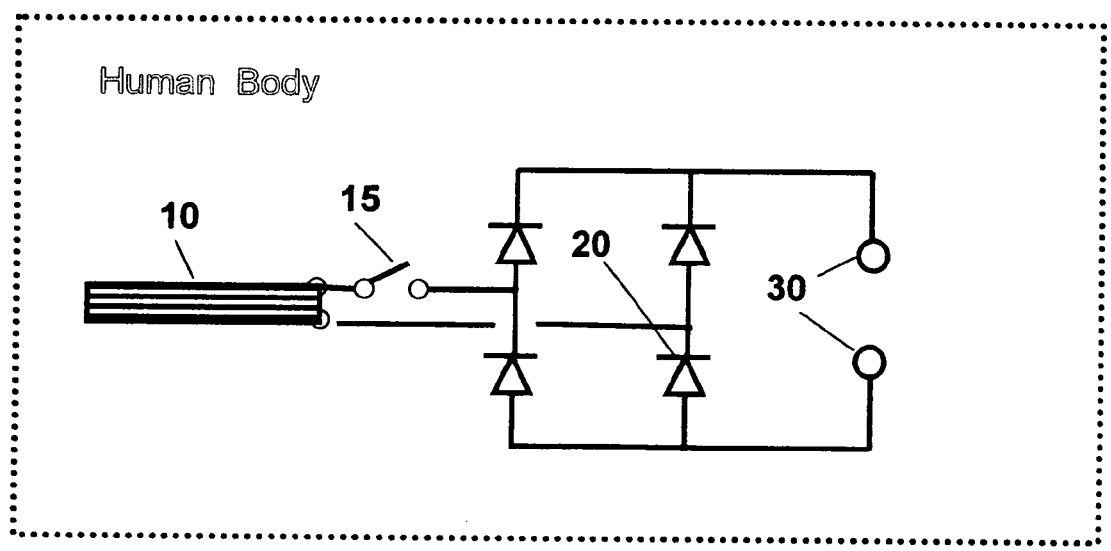
FIG. 2 illustrates a device comprising a piezoelectric element for generating an electrical potential in response to a motion of a human body, and an electrical circuit consisting of an on-off switch, a full wave rectifier bridge and electrodes for contact with a human body.

An article of the invention comprising the device of the invention illustrated in FIG. 2 is worn on a part of a human body selected from the neck, shoulder, elbow, wrist, hand, back, knee, ankle, chest, abdomen, leg and foot. The article of the invention may be attached to the body part by an elasticized fabric (not shown). The piezoelectric element of the device 10 is actuated by the motion of that body part and produces an electrical potential. The piezoelectrical element is connected through an optional on-off switch 15 to a full-wave rectifier bridge consisting of low leakage diodes 20 and thence to a pair of electrodes 30. When the circuit is closed, random motion of the body part produces an electrical potential at the electrodes 30 of full-wave rectified pulses of random frequency and amplitude. The electrodes 30 are in contact with a human body that receives the electrical power. The human body actuating the piezoelectric element need not be the human body in contact with the electrodes, as for example where the article is a massage glove.

Example 3

Figure 3:
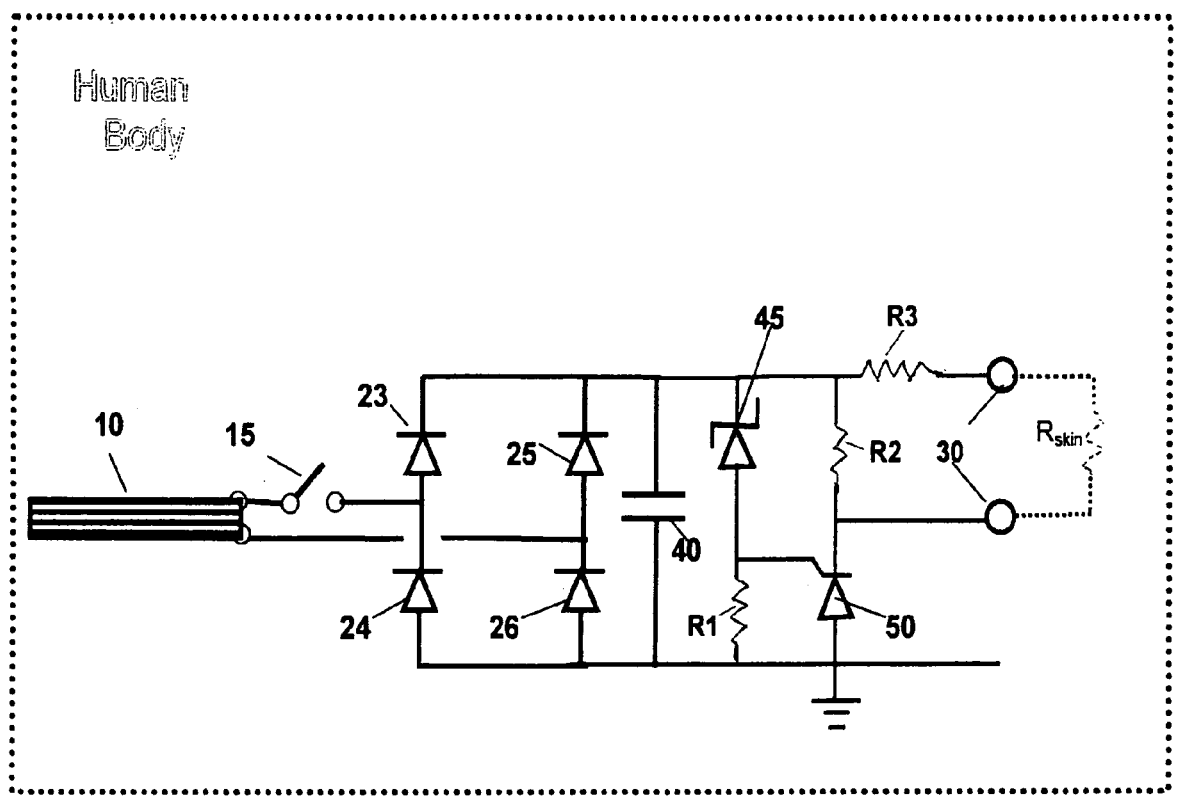
FIG. 3 illustrates a device comprising a piezoelectric element for generating an electrical potential in response to a motion of a human body, an electrical circuit consisting of on-off switch, a full wave rectifier bridge, a storage capacitor, a Zener diode, a silicon controlled rectifier, appropriate resistors and electrodes for contact with a human body.

An article of the invention comprising the device of the invention illustrated in FIG. 3 is worn on a part of a human body selected from the neck, shoulder, elbow, wrist, hand, back, knee, ankle, chest, abdomen, leg and foot. The article of the invention may be attached to the body part by an elasticized fabric (not shown). The piezoelectric element of the device 10 is actuated by the motion of that body part and produces an electrical potential. The piezoelectric element is connected to a circuit that stores and modifies the electrical potential and delivers it to electrodes 30. The electrodes 30 are in contact with a human body that receives the electrical power. The human body actuating the piezoelectric element need not be the human body in contact with the electrodes.

The circuit comprises an optional on-off switch 15, diodes 23, 24, 25, 26, capacitor 40, a Zener diode 45, a silicon controlled rectifier (SCR) 50 and resisters R1, R2, and R3. Preferred elements for this circuit are shown in Table I below.

Low leakage diodes 23, 24, 25, 26 form a full-wave bridge rectifier that converts the alternating current output from the piezoelectric element to a direct current. The rectified input current is accumulated in capacitor 40: a metallized polyester film capacitor selected for its low loss energy storage capability. When the voltage in capacitor 40 rises to the breakdown potential of the Zener diode 45, the Zener starts to conduct current into resistor R1. When the capacitor voltage exceeds the sum of the Zener breakdown voltage and the SCR gate threshold voltage, the SCR 50 triggers and discharges the capacitor 40 into the resistive load comprised of resistors R2, R3 plus the skin impedance of the human body.

Random motion of the body part causes pulses of electrical energy to be transmitted to the electrodes 30. The pulse repetition rate will be random, but it will be of constant initial magnitude. The decay rate of the pulse will depend on the rate at which charge is delivered to the capacitor, the capacitance of the capacitor and on the resistance between the electrodes.

The circuit parameter values can easily be modified to provide the most desirable skin stimulus.

TABLE I

| Circuit Element | Description | Manufacturer | Website |
|---|---|---|---|
| 10 | Ceramic Fiber Piezoelectric Transducer | Advanced Cerametrics Inc. | www.advancedcerametrics.com |
| 23, 24 | Diode Array, Low Leakage Silicon Switching | Central Semiconductor Corp., Part No. CMPD6001S | www.centralsemi.com |
| 25, 26 | Diode Array, Low Leakage Silicon Switching | Central Semiconductor Corp., Part No. CMPD6001S | www.centralsemi.com |
| 40 | Capacitor, 1 µF, Metallized Polyester Film | Vishay | www.vishay.com/capacitors/polyester |
| 45 | Zener Diode, 47 volt | Central Semiconductor Corp., Part No CMPZ5261B | www.centralsemi.com |
| 50 | SCR, Sensitive Gate, 200PRV | Central Semiconductor Corp., Part No CMPS5062 | www.centralsemi.com |
| R1 | Resistor, 4.7K, 5%, 0.1 W Thick Film or Metal Film | Any | |
| R2 | Resistor, 4.7K, 5%, 0.25 W | Any | |
| R3 | Resistor, 10K, 5%, 0.25 W | Any | |

The capacitance value of the capacitor 40 affects both the time-to-trigger (repetition rate) and the length of the pulses delivered. If the capacitance is increased, the circuit will take longer to achieve the trigger voltage that is set by the Zener 45 breakdown voltage. Greater capacitance will also lengthen the output pulse waveform and increase the energy delivered to the skin per pulse. Decreasing the capacitance has the opposite effects on the time-to-trigger, the pulse waveform and the energy.

The Zener 45 breakdown voltage sets the threshold at which the SCR 50 will fire. Lowering the Zener breakdown voltage shortens the time-to-trigger and also lowers the output pulse peak voltage and its duration. Raising the Zener voltage has the opposite effects on the time-to-trigger and the output pulse peak voltage and duration.

The SCR 50 preferably has very low gate-to-cathode and anode-to-cathode leakage currents. Preferably, it is also a sensitive gate device, requiring a low gate current to trigger.

Resistor R1 is necessary to discharge the SCR 50 gate capacitance, removing triggering energy in time to allow the SCR to stop conducting when its anode-to-cathode voltage decays to near zero. If the resistance R1 is too small, when the Zener 45 begins to conduct, the Zener current will not develop a high enough gate voltage across resistor R1 and the SCR 50 will not trigger. On the other hand, if resistance R1 is too large, the SCR 50 may trigger once and not recover from the triggered state until all power is removed. This is because the charge stored in the gate junction of the SCR may not have sufficiently discharged when the next possible triggering event has occurred. Therefore, if resistance R1 is too large, the SCR 50 may remain in the on state sending all of the input power into the electrodes 30 with an unmodified waveform.

Resistor R2 in parallel with the series combination of resistor R3 and the skin impedance determines the discharge time constant of the capacitor 40 and the output waveshape as:

Time constant, sec=$R_{eq}C$ where:

$$R_{eq} = \frac{R_2(R_3 + R_{skin})}{R_2 + R_3 + R_{skin}}$$

R2 is preferably smaller than the series combination of R3 and the skin impedance. If the resistance of R2 is increased or decreased, the discharge time is lengthened or shortened respectively. Increasing or decreasing the discharge time directly increases or decreases the energy delivered to the skin per pulse. R2 also serves to lessen the effect of variations in skin impedance on circuit performance and energy delivered. The output network, R2, R3, and $R_{skin}$, form a classic Π-section (Pi-section) Attenuator that attenuates the effect of high skin impedance variability on the rest of the circuit.

R3 serves to limit the energy delivered to the skin. Increasing the resistance of R3 reduces the energy delivered to the skin, and has a minor effect on increasing the discharge time of the capacitor 40. R3, being directly in series with the electrodes 30 is the major human safety element in the circuit.

Example 4

Figure 4:
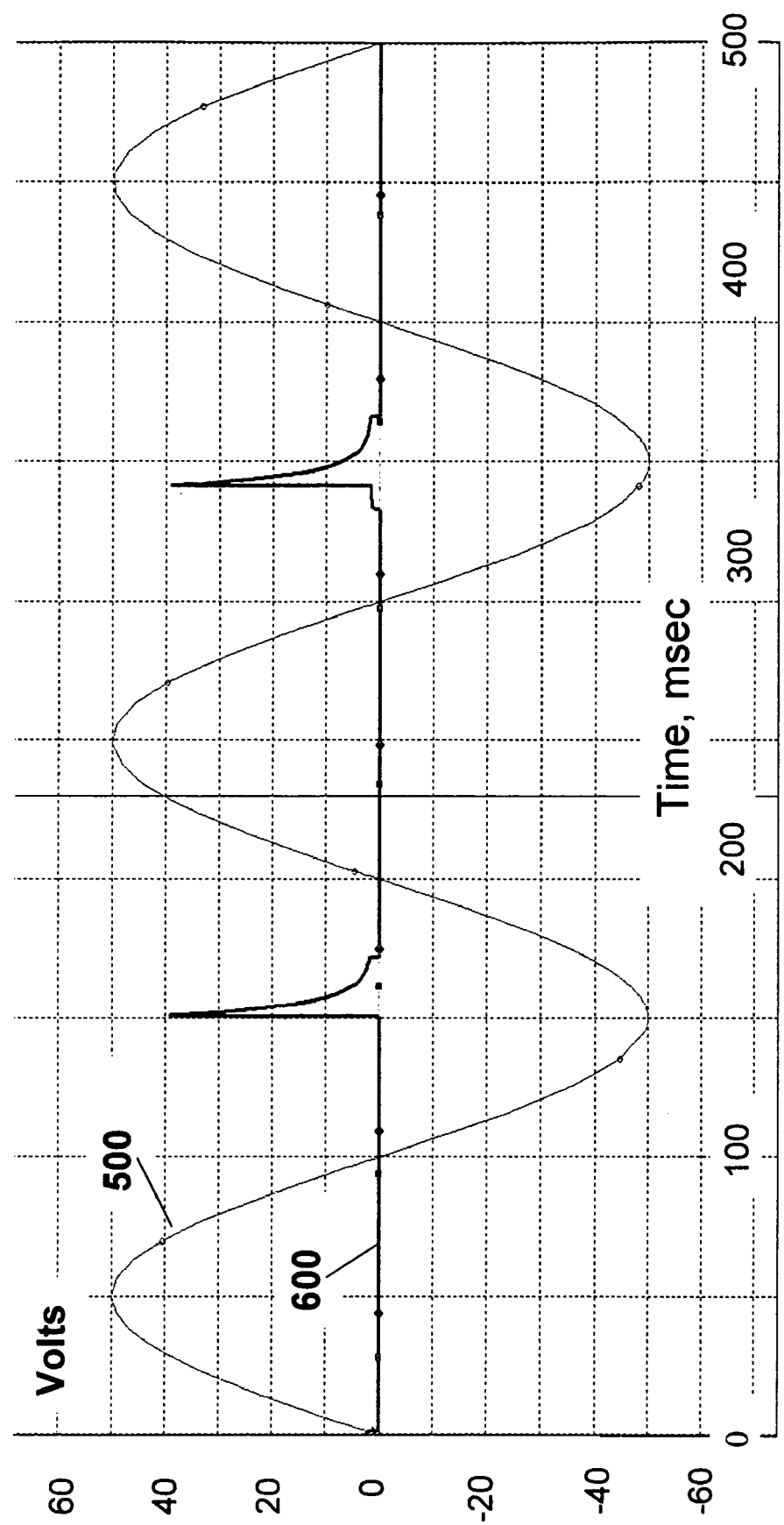
FIG. 4 illustrates a plot of the input and output of the device of FIG. 3 under a sinusoidal mechanical stress of 5 Hz frequency.
Figure 5:
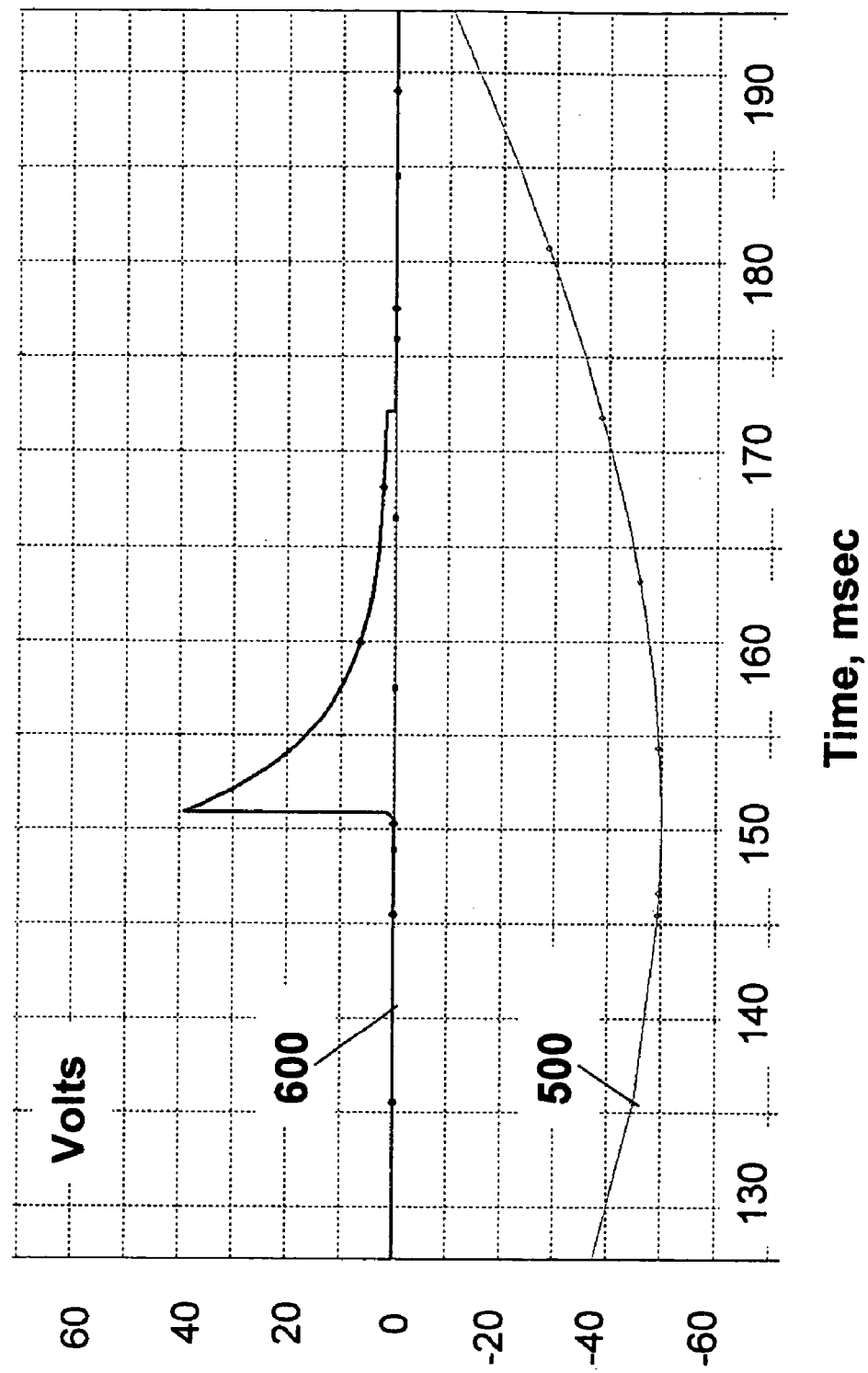
FIG. 5 is the same plot as FIG. 4 on an expanded time scale.

The device described in Example 3 and FIG. 3 was simulated using the "B2 Spice A/D 2000 Workshop" electronic modeling software from Beige Bag Software, Inc., Ann Arbor, Mich. For simplicity, it was assumed that the piezoelectric element delivered a 500 micoroampere sinusoidal input current at a frequency of 5 Hz into the circuit. The skin impedance was taken as 50,000 ohms. The input waveform 500 and the waveform of the output into the skin impedance 600 are shown in FIG. 4. An expanded time scale is shown in FIG. 5. It was found that the circuit will deliver a nominal 40 volt peak pulse into the skin impedance, with a half-amplitude duration of 3 milliseconds. This equates to a 32 milliwatt pulse having an energy of about 96 microJoules (microwatt-seconds).

It will be recognized that in the actual application, the piezoelectric element will be actuated by human motion and its output will be essentially random rather than strictly periodic or sinusoidal.

Example 5

An inventive device illustrated in any one of the foregoing FIGS. 2-3 consisting of a piezoelectric element for generating an electrical potential, an electrical circuit for collection, storage, and modification of that potential and at least one pair of oppositely polarized electrodes is embedded in a condom and placed on a penis. At least one pair of oppositely polarized electrodes is on one of the inner or outer surface of the condom in electrical contact with one or two human bodies.

The piezoelectric element is actuated by the act of intercourse and an electrical potential is transmitted to one or both human bodies.

Having thus described the invention in rather full detail, it will be understood that such detail need not be strictly adhered to but that further changes, modifications and uses may suggest themselves to one skilled in the art, all falling with the scope of the invention as defined by the subjoined claims.

What is claimed is:

1. A self-contained device for applying an electrical potential to a skin surface of a human body comprising:
   a) a piezoelectric element capable of generating an electrical potential in response to a mechanical stress or strain of said piezoelectric element caused by motion of a human body;
   b) an electrical circuit connected to said piezoelectric element for collection, storage or modification of said electrical potential; connected to
   c) at least two spaced-electrode means of opposite polarity for applying said electrical potential to a skin surface of a human body for transdermal administration of drugs, treatment of pathologies, electrocicatirization of wounds or injuries to promote healing, transcutaneous electrical nerve stimulation to relieve pain and other applications;
   d) said device being embedded in a fabric capable of being worn on a part of a human body selected from the neck, shoulder, elbow, wrist, hand, back, knee, ankle, chest, abdomen, penis, leg and foot, the piezoelectric element of said device being capable of being mechanically stressed or strained by motion of said part of the body, and the electrodes of said device capable of being in contact with a skin surface of a human body.

2. The device of claim 1, wherein said piezoelectric element is comprised of at least one member of the group consisting of PZT or lead zirconium titanate), lead niobate, pure or co-doped barium titanate, sodum bismuth titanate, lead based ceramics doped with lanthanum, tin or niobium, quartz, lithium niobate, lithium tantalate, polyvinylidene fluoride, polytrifluoroethylene, polytetrafluoroethylene, polyvlylldene cyanide, and polyvinyl acetate.

3. The device of claim 1, wherein the piezoelectric element is a composite comprised of one or more planar layers of parallel aligned piezoelectric fibers embedded in a matrix.

4. The device of claim 3, wherein the piezoetectric fibers are selected from the group consist of PZT or lead zirconium titanate, lead niobate, barium titanate, pure or co-doped sodium bismuth titanate.

5. The device of claim 3, wherein said matrix is a rigid polymeric material having a modulus of elasticity as measured by ASTM D638 greater than about 200,000 psi or 1,380 MPa.

6. The device of claim 3, wherein said matrix is a polymeric material having a modulus of elasticity as measured by ASTM D638 less than about 6000 psi (41.3 MPa).

7. The device of claim 1, wherein the electrical potential across said electrodes generated by a random motion of a human body has a full wave rectified waveform of random frequency and amplitude.

8. The device of claim 1, wherein the electrical potential across said electrodes generated by a random motion of a human body has a pulsed waveform of random frequency.

9. The device of claim 8, wherein the electrical energy per pulse is from about 1 to about 750 microJoules.

10. The device of claim 8, wherein the electrical energy per pulse is from about 1 to about 100 microJoules.

11. The device of claim 1, wherein the electrical potential across said electrodes generated by a random motion of a human body has a pulsed waveform of random frequency and essentially constant pulse amplitude.

12. The device of claim 11, wherein the electrical energy per pulse is from about 1 to about 750 microJoules.

13. The device of claim 11, wherein the electrical energy per pulse is from about 1 to about 100 microJoules.

14. The device of claim 1 wherein said electrical circuit for collection storage or modification of said electrical potential is one selected from the group consisting of:
   an optional on-off switch 15 connected on one side to said piezoelectric element and connected on the other side to a full-wave rectifier bridge consisting of low leakage diodes 20 and thence to said electrodes, as illustrated in FIG. 2; and
   an optional on-off switch 15 connected on one side to said piezoelectric element and connected on the other side on the other side to a full-wave rectifier bridge consisting of low leakage diodes 23-26, and thence to a capacitor 40, a Xener diode 45, resistances R1-R3, SCR 50, and thence to said electrodes as illustrated in FIG. 3.

15. The device of claim 1, wherein a maximum electrical potential generated by said piezoelectric element is from about 1 to about 500 volts.

16. The device of claim 1, wherein a maximum electrical potential across said electrodes is from about 10 volts to about 40 volts.

17. The device of claim 1, wherein an electrical power capable of being deliver to a human body by said device is from about 0.05 milliwatts to about 250 milliwatts.

18. The device of claim 1, wherein an electrical power capable of being delivered to a human body by said device is from about 0.05 milliwatts to about 100 milliwatts.

19. The device of claim 1, wherein the distance between electrodes of opposite polarity is from about 0.125 inch or 0.317 cm to about 10 inches or 25.4 cm.

20. The device of claim 1, where the total area of electrodes of a given polarity, measured in square centimeters, is at least 1.9 times the electrical power capability of said device measured in watts.

21. The device of claim 1, wherein said device is embedded in a glove.

22. The device of claim 21 comprising a massage glove with said electrodes exposed on the outer surface of the palm of said glove.

23. The device of claim 1 wherein at least a part of said fabric is one of an elastic material or an elasticized fabric.

24. A method of applying an electrical potential to a skin surface of a human comprising the step of:
   placing a device as described in claim 1 on a body part such that the piezoelectric array of said device is mechanically stressed or strained by the motion of the body part and the electrodes of said device are In electrical contact with a skin surface of a human body.

25. A method of applying an electrical potential to a surface of a human body comprising the steps of:
   a) embedding a device as described in claim 1 in a condom having an inner and outer surface; and
   b) placing said condum on a penis such that the piezoelectric array of said device is mechanically stressed or strained by the act of intercourse and at least two oppositely polarized electrodes of said device are on at least one of said inner or outer surface.

26. A self-contained device for applying an electrical potential to a skin surface of a human body comprising:

a) a piezoelectric element capable of generating an electrical potential in response to a mechanical stress or strain of said piezoelectric element caused by motion of a human body; wherein said piezoelectric element Is a composite comprised of one or more planar layers of parallel aligned piezoelectric fibers embedded in a matrix of a rigid polymeric material having a modulus of elasticity as measured by ASTM D0636 greater than about 200,000 psi or 1,389 MPa; and wherein said piezoelectric fibers are selected from the group consisting of: PZT or lead zirconium titanate; lead niobate; barium titanate; and pure or do-doped sodium bismuth titanate;

b) an electrical circuit connected to said piezoelectric element for collection, storage or modification of said electrical potential, said electrical circuit selected from the group consisting of:
  i. an optional on-off switch 15 connected on one side to said piezoelectric element and connected on the other side to a full-wave rectifier bridge consisting of low leakage diodes 20 and thence to electrodes 30 for applying said electrical potential to a skin surface of a human body for transdermal administration of drugs, treatment of pathologies, electrocicatirization of wounds or injuries to promote healing, transcutaneous electrical nerve stimulation to relieve pain and other applications; as illustrated in FIG. 2; and
  ii. an optional on-off switch 15 connected on one side to said piezoelectric element and connected on the other side to a full-wave rectifier bridge consisting of low leakage diodes 23-26, and then to a capacitor 40, a Xener diode 45, resistances R1-R3, SCR 50 and thence to electrodes 30 for applying said electrical potential to a skin surface of a human body for transdermal administration of drugs, treatment of pathologies, electrocicatirization of wounds or injuries to promote healing, transcutaneous electrical nerve stimulation to relieve pain and other applications; as illustrated in FIG. 3;

c) said device being capable of being worn on a part of a human body selected from the neck, shoulder, elbow, wrist, hand, back, knee, ankle, chest, abdomen, penis, leg and foot, the piezoelectric element of said device being capable of being mechanically stressed or strained by motion of said part of the body, and the electrodes of said device capable of being in contact with a skin surface of a human body.

27. The device of claim 26, wherein a maximum electrical potential generated by said piezoelectric element is from about 1 to about 500 volts.

28. The device of claim 26, wherein a maximum electrical potential across said electrodes is from about 10 volts to about 40 volts.

29. The device of claim 26, wherein an electrical power capable of being deliver to a human body by said device is from about 0.05 milliwatts to about 250 milliwatts.

30. The device of claim 26, wherein an electrical power capable of being delivered to a human body by said device is from about 0.05 milliwatts to about 100 milliwatts.

31. The device of claim 26, wherein the distance between electrodes of opposite polarity is from about 0.125 inch or 0.317 cm to about 10 inches or 25.4 cm.

32. The device of claim 26, where the total area of electrodes of a given polarity, measured in square centimeters, is at least 1.9 times the electrical power capability of said device measured in watts.

33. The device of claim 26, wherein said device is embedded in a condom.

34. A self-contained device for applying an electrical potential to a skin surface of a human body comprising:
  d) a piezoelectric element capable of generating an electrical potential in response to a mechanical stress or strain of said piezoelectric element caused by motion of a human body;
  e) an electrical circuit connected to said piezoelectric element for collection, storage or modification of said electrical potential; connected to
  f) at least two spaced-electrode means of opposite polarity for applying said electrical potential to a skin surface of a human body;
  g) said device being embedded in a condum.

* * * * *